United States Patent [19]
Rao et al.

[11] Patent Number: 6,028,026
[45] Date of Patent: Feb. 22, 2000

[54] CUBIC CHROMIUM TRIFLUORIDE AND ITS USE FOR HALOGENATED HYDROCARBON PROCESSING

[75] Inventors: V. N. Mallikarjuna Rao, Wilmington, Del.; Munirpallam A. Subramanian, Kennett Square, Pa.

[73] Assignee: E. I. du Pont de Nemours and Company, Wilmington, Del.

[21] Appl. No.: 09/136,805

[22] Filed: Aug. 20, 1998

Related U.S. Application Data

[60] Provisional application No. 60/056,792, Aug. 25, 1997.

[51] Int. Cl.[7] ............................ B01J 27/12; B01J 27/132
[52] U.S. Cl. ......................... 502/228; 423/489; 423/492; 570/163; 570/168; 570/170
[58] Field of Search ..................................... 423/489, 492; 502/228; 570/123, 164, 165, 166, 168, 163, 170, 176

[56] References Cited

U.S. PATENT DOCUMENTS

| | | | |
|---|---|---|---|
| 2,599,631 | 6/1952 | Harmon | 260/653 |
| 2,745,886 | 5/1956 | Ruh et al. | 423/489 |
| 3,673,113 | 6/1972 | Naito et al. | 502/228 |
| 4,034,070 | 7/1977 | Wojtowicz et al. | 428/489 |
| 4,053,530 | 10/1977 | Schindel | 570/170 |
| 4,465,786 | 8/1984 | Zimmer et al. | 502/228 |
| 4,741,893 | 5/1988 | Watanabe et al. | 423/489 |
| 5,461,177 | 10/1995 | Manzer et al. | |

FOREIGN PATENT DOCUMENTS

| | | | |
|---|---|---|---|
| 2900854 | 7/1979 | Germany | 423/489 |
| WO 93/25506 | 12/1993 | WIPO | |
| WO 94/06558 | 3/1994 | WIPO | |
| WO 96/05157 | 2/1996 | WIPO | |
| WO 97/07052 | 2/1997 | WIPO | |

OTHER PUBLICATIONS

L. E. Manzer et al., *Adv. Catal.*, 39, 329–350, 1993 No month.

*Ullman's Encyclopedia of Industrial Chemistry*, Fifth Ed., vol. A7, 83 No date.

Daniel et al, "Raman–Scattering . . . Short–Range–Order Force Constants", Physical Review B, vol. 42, No. 16, pp. 10545–10552, Dec. 1990.

Shrivastava, K.N, "Theory of the $\pi$–Electron . . . in a Cubic Fluoride Lattia", Physical Review B, vol. 20, No. 12, pp. 5375–5378, Dec. 1979.

*Primary Examiner*—Ngoc-Yen Nguyen

[57] ABSTRACT

This invention provides a crystalline chromium fluoride having a cubic crystal structure (i.e., chromium trifluoride having an X-ray diffraction powder pattern as shown in Table I); and a catalytic composition comprising cubic chromium trifluoride. This invention also provides a process for changing the fluorine content of halogenated hydrocarbons containing from one to six carbon atoms, in the presence of a chromium-containing catalyst. The process is characterized by the chromium-containing catalyst comprising cubic chromium trifluoride.

9 Claims, No Drawings

CUBIC CHROMIUM TRIFLUORIDE AND ITS USE FOR HALOGENATED HYDROCARBON PROCESSING

This application claims the priority benefit of U.S. Provisional Application Ser. No. 60/056,792, filed Aug. 25, 1997.

FIELD OF THE INVENTION

This invention relates to chromium-containing catalysts and their use in the processing of halogenated hydrocarbons.

BACKGROUND

A number of chlorine-containing halocarbons are considered to be detrimental toward the Earth's ozone layer. There is a world-wide effort to develop materials having lower ozone depletion potentials that can serve as effective replacements. For example, the hydrofluorocarbon, 1,1,1,2-tetrafluoroethane (HFC-134a) is being used as a replacement for dichlorodifluoromethane (CFC-12) in refrigeration systems. There is a need for manufacturing processes that provide fluorocarbons that contain less chlorine or no chlorine.

Numerous processes have been developed for changing the fluorine content of halogenated hydrocarbons. Various catalysts have been proposed for use in facilitating processes such as fluorination. See, e.g., L. E. Manzer et al., Adv. Catal. (39) pp. 329–350 (1993).

Chromia catalysts, which include crystalline $Cr_2O_3$, amorphous phases and mixtures, have been widely used for halogenated hydrocarbon processing. Typically, the activity of these chromia catalysts decrease with time during their use in hydrofluorination processes. WO 94/06558 discloses that a major cause of this deactivation is the conversion of chromia to chromium trifluoride. $CrF_3$ has been reported to form rhombohedral crystals (see e.g., Ullman's Encyclopedia of Industrial Chemistry, Fifth Ed., Vol. A7, p. 83). There is an ongoing interest in developing efficient catalysts for changing the fluorine content of halogenated hydrocarbons.

SUMMARY OF THE INVENTION

This invention provides a crystalline chromium fluoride having a cubic crystal structure (i.e., chromium trifluoride having an X-ray diffraction powder pattern as shown in Table I); and a catalytic composition comprising cubic chromium trifluoride. This invention also provides a process for changing the fluorine content of halogenated hydrocarbons containing from one to six carbon atoms, in the presence of a chromium-containing catalyst. The process is characterized by the chromium-containing catalyst comprising cubic chromium trifluoride.

DETAILED DESCRIPTION

This invention involves cubic chromium trifluoride, a composition having an X-ray diffraction powder pattern as shown in Table I, as follows:

TABLE I

Powder X-ray diffraction Data for Cubic-$CrF_3$

| d spacing (Å) | Relative intensity[a] | H | K | L |
|---|---|---|---|---|
| 5.8888 | VS[b] | 1 | 1 | 1 |
| 3.0674 | S[c] | 3 | 1 | 1 |
| 2.9423 | M[d] | 2 | 2 | 2 |
| 2.0818 | W[e] | 4 | 2 | 2 |
| 1.9547 | W[e] | 5 | 1 | 1 |
| 1.7991 | M[d] | 4 | 4 | 0 |

[a] as recorded at room temperature using a conventional diffractometer such as SCINTAG (PAD IV) diffractometer with copper k-alpha radiation
[b] VS means very strong (e.g., a relative intensity of about 100)
[c] S means strong (e.g., a relative intensity of about 46)
[d] M means moderate (e.g., a relative intensity of about 33 and about 14 for d spacing of 2.9423 and 1.7991, respectively)
[e] W means weak (e.g., a relative intensity of about 7 and about 4 for d spacing of 2.0818 and 1.9547, respectively)

Cubic chromium trifluoride may be prepared from $CrF_3 \cdot XH_2O$, where X is 3 to 9, preferably 4, by heating in air or an inert atmosphere (e.g., nitrogen or argon) at 350° C. to 400° C. for 3 to 12 hours, preferably 3 to 6 hours. The color of cubic chromium trifluoride is dark green.

Cubic chromium trifluoride is useful by itself and together with other chromium compounds, as a catalytic material. Of note are catalyst compositions comprising chromium wherein at least 10% of the chromium is in the form of cubic chromium trifluoride, particularly catalyst compositions wherein at least 25% of the chromium is in the form of cubic chromium trifluoride, and especially catalyst compositions wherein at least 60% of the chromium is in the form of cubic chromium trifluoride. The chromium, including the cubic chromium trifluoride can be supported on and/or physically mixed with materials such as carbon, aluminum fluoride, fluorided alumina, lanthanum fluoride, magnesium fluoride, calcium fluoride, zinc fluoride and the like. Preferred are combinations including cubic chromium trifluoride in combination with magnesium fluoride and/or zinc fluoride. Chromium trifluoride catalyst which consists essentially of cubic chromium trifluoride can also be prepared and used in accordance with this invention.

The cubic chromium trifluoride-containing catalyst may be of various physical shapes, including for example, pellets, powders and granules.

Included in this invention is a process for increasing the fluorine content of a saturated or olefinic halogenated hydrocarbon starting material of the formula $C_nH_aCl_bF_c$, wherein n is an integer from 1 to 6, a is an integer from 0 to to 12, b is an integer from 0 to 13 and c is an integer from 0 to 13, provided that b is at least 1 when the compound is saturated, by reacting said compound with HF in the vapor phase; and a process for the disproportionation of a compound having the formula $C_pH_gF_hCl$, where p is an integer from 1 to 2, g is an integer from 1 to 3 and h is an integer from 1 to 4. These processes are respectively characterized by reacting the $C_nH_aCl_bF_c$ compound with HF and conducting the disproportionation of the $C_pH_gF_hCl$ compound, in the presence of a catalyst comprising cubic chromium trifluoride.

The vapor phase contact of the cubic chromium trifluoride-containing catalyst with the HF and the saturated or olefinic halogenated hydrocarbons of the formula $C_nH_aCl_bF_c$, wherein n is an integer from 1 to 6, a is an integer from 0 to to 12, b is an integer from 0 to 13 and c is an integer from 0 to 13, is typically conducted at from about 150° C. to 500° C. For saturated compounds the contact is preferably from about 175° C. to 400° C., more preferably at from about 200° C. to about 350° C. The contact time is typically from about 1 to about 120 seconds (e.g., from about 5 to about 60 seconds). The amount of HF ordinarily should be at least a stoichiometric amount. Typically, the molar ratio of HF to the said compounds of the formula $C_nH_aCl_bF_c$ can range from about 0.5:1 to about 100:1, preferably about 2:1 to 50:1, and more preferably from about 3:1 to 10:1. In general, with a given catalyst composition, the higher the temperature and the longer the contact time, the greater is the conversion to fluorinated products. The above variables can be balanced, one against the other, so that the formation of higher fluorine substituted products is maximized.

Examples of olefinic compounds which may be reacted with HF in the presence of the catalyst of this invention include $CHCl=CCl_2$, $CCl_2=CCl_2$, $CCl_2=CH_2$, $CCl_2=CF_2$, $CHF=CF_2$, $CF_2=CH_2$, $CF_2=CFCl$, $CCl_2=CClCCl_3$, $CF_3CCl=CF_2$, $CF_3CH=CF_2$, $CF_3CF=CHF$ and $CCl_3CCl=CClCCl_3$. Of note is a catalytic process for producing 2-chloro- 1,1,1-trifluoroethane (HCFC-133a) by the fluorination of a trihaloethene of the formula $CX_2=CHCl$ wherein each X is chlorine or fluorine. Starting materials include trichloroethene, 1,2-dichlorofluoroethene and 1-chloro-2,2-difluoroethene. Trichloroethene is preferred. HCFC-133a is produced by reacting the above unsaturated compounds with HF in the vapor phase in the presence of the catalyst of this invention. The reaction of the above trihaloethenes with HF in the presence of the catalyst of the instant invention is preferably conducted at about 150° C. to 350° C., more preferably about 175° C. to 250° C. Oxygen may be co-fed, if desired.

Also of note is a catalytic process for producing 2,2-dichloro-1,1,1-trifluoroethane (i.e., $CHCl_2CF_3$ or HCFC-123), 1,1,1,2-tetrafluorochloroethane i.e., $CHClFCF_3$ or HCFC-124) and pentafluoroethane (i.e., $CHF_2CF_3$ or HFC-125) by the fluorination of a tetrahaloethene of the formula $C_2Cl_{4-x}F_x$, wherein x equals 0 to 3 in the presence of the chromium trifluoride catalyst of this invention. Starting materials include $CCl_2=CCl_2$, $CClF=CCl_2$, $CClF=CClF$, $CF_2=CCl_2$ and $CF_2=CClF$. Tetrachloroethene is preferred. HCFC-123, HCFC-124 and/or HFC-125 are produced by reacting the above unsaturated compounds with HF in the vapor phase in the presence of the catalyst of this invention.

Examples of saturated compounds which may be reacted with HF in the presence of the catalyst of this invention include $CH_2Cl_2$, $CHCl_3$, $C_2Cl_6$, $C_2Cl_5F$, $C_2Cl_4F_2$, $C_2Cl_3F_3$, $C_2Cl_2F_4$, $C_2ClF_5$, $C_2HCl_5$, $C_2HCl_4F$, $C_2HCl_3F_2$, $C_2HCl_2F_3$, $C_2HClF_4$, $C_3HCl_7$, $C_3HCl_6F$, $C_3HCl_5F_2$, $C_3HCl_4F_3$, $C_3HCl_3F_4$, $C_3HCl_2F_5$, $C_3H_2Cl_5F$, $C_3H_2Cl_4F_2$, $C_3H_2Cl_3F_3$, $C_3H_2Cl_2F_4$, $C_3H_2ClF_5$ and $C_3H_2Cl_6$ (e.g., $CCl_3CH_2CCl_3$). Mixtures of saturated compounds may also be used (e.g., a mixture of $CH_2Cl_2$ and $CCl_3CF_3$; or a mixture of $CCl_2FCClF_2$ and $CCl_3CF_3$). Of note are catalytic processes for reacting 1,1,1-trichloro-2,2,2-trifluoroethane (i.e., $CCl_3CF_3$ or CFC-113a), or reacting dichloromethane, with HF, in the vapor phase in the presence of the catalyst of this invention. For the reaction of CFC-113a with HF to yield $CCl_2FCF_3$ (CFC-114a), the $HF:CCl_3CF_3$ ratio can vary widely. The HF:CFC-113a molar ratio should be at least 0.5:1, but is preferably within the range of from about 2:1 to about 10:1.

For the reaction of dichloromethane to yield difluoromethane (i.e., $CH_2F_2$ or HFC-32), the molar ratio of HF to $CH_2Cl_2$ preferred ranges are from about 1:1 to about 10:1. The reaction temperature normally ranges from about 180° C. to about 375° C. (e.g., from about 200° C. to about 350° C.).

For the reaction of mixtures of $CH_2Cl_2$ and $CCl_3CF_3$ to yield mixtures of $CH_2F_2$ and $CCl_2FCF_3$, the molar ratio of HF added to the total amount of $CH_2Cl_2$ and $CCl_3CF_3$ starting material typically ranges from about 0.5:1 to about 10:1, and is preferably from about 1:1 to about 8:1. Typically, the molar ratio of $CH_2Cl_2$ to $CCl_3CF_3$ in mixtures ranges from about 1:9 to about 9:1.

For the reaction of mixtures of $CCl_2FCClF_2$ and $CCl_3CF_3$ to yield mixtures of $CClF_2CClF_2$ and $CCl_2FCF_3$, the molar ratio of HF added to the total amount of $CCl_2FCClF_2$ and $CCl_3CF_3$ starting material typically ranges from about 1:1 to about 10:1, and is preferably from about 1:1 to about 5:1. Typically, the molar ratio of $CCl_2FCClF_2$ to $CCl_3CF_3$ in mixtures ranges from about 1:99 to about 9:1. The reaction of $C_2Cl_3F_3$ with HF in the presence of the catalyst of this invention can be used to obtain mixtures enriched in the asymmetric $C_2Cl_2F_4$ (i.e., $CCl_2FCF_3$) isomer.

Suitable hydrochlorofluorocarbons for disproportionation include $CH_2ClF$, $CH_3CClF_2$, and $CHClFCF_3$. The products of the disproportionation reactions are respectively, $CH_2F_2$ and $CH_2Cl_2$, $CH_3CF_3$ and $CH_2=CCl_2$, and $CHCl_2CF_3$ and $CHF_2CF_3$.

Pressure is not critical. Atmospheric and superatmospheric pressures are the most convenient and are therefore preferred.

The reaction products are separated by conventional techniques, such as distillation. Some of the reaction products will have desired properties for commercial use. For example $CCl_3CF_3$ (CFC-113a) can be used to prepare CFC-114a which can then be converted to $CH_2FCF_3$ (HFC-134a) by hydrodechlorination.

The process of this invention can be carried out readily in the vapor phase using well known chemical engineering practices.

The reaction zone and its associated feed lines, effluent lines and associated units should be constructed of materials resistant to hydrogen fluoride and hydrogen chloride. Typical materials of construction, well-known to the fluorination art, include stainless steels, in particular of the austenitic type, the well-known high nickel alloys, such as Monel® nickel-copper alloys, Hastelloy® nickel-based alloys and, Inconel® nickel-chromium alloys, and copper-clad steel.

Without further elaboration, it is believed that one skilled in the art can, using the description herein, utilize the present invention to its fullest extent. The following specific embodiments are, therefore, to be construed as merely illustrative, and do not constrain the remainder of the disclosure in any way whatsoever.

EXAMPLES

Example 1

Preparation of Cubic Chromium Trifluoride

Commercial rhombohedral $CrF_3 \cdot 4H_2O$ (about 3 g) was placed in a gold container and heated to 400° C. for 3–12 hours in air. The product was recovered and characterized. Powder x-ray diffraction measurements were recorded at room temperature using a SCINTAG (PAD IV) commercial diffractometer with copper k-alpha radiation, and indicated that the crystal structure of the product formed can be indexed as cubic with a lattice parameter of 10.201 Å (Table 2). The samples were weighed before and after the experiments. Weight loss measurements showed the compound formed at 400° C./6 hours is $CrF_3$ (Table 1) as shown in the equation

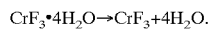
$$CrF_3 \cdot 4H_2O \rightarrow CrF_3 + 4H_2O.$$

(Weight loss observed: 39.8%, Weight loss calculated 39.77%). The intensities of X-ray diffraction data show the compound has a face-centered cubic unit cell with space group Fd3m.

TABLE 1

| Temp./time | Obs. weight loss | Phase formation |
|---|---|---|
| 200° C./12 hr | 25.6% | Amorphous |
| 250° C./6 hr | 28.4 | Amorphous |
| 300° C./6 hr | 31.1% | Amorphous + Cubic |
| 350° C./12 hr | 39.3% | Cubic |
| 400° C./3 hr | 38.6% | Cubic |
| 400° C./6 hr | 39.8% | Cubic |
| 400° C./12 hr | 51.0% | Amorphous + Cubic |
| 500° C./3 hr | 52.4% | $CrOF_2$ + $Cr_2O_3$ + amor. + Cubic |

TABLE 2

Powder X-ray diffraction Data for Cubic-$CrF_3$
($CrF_3 \cdot 4H_2O$, 400° C./6 hours)

| d spacing (Å) | Relative Intensity | H | K | L |
|---|---|---|---|---|
| 5.8888 | 100 | 1 | 1 | 1 |
| 3.0674 | 46 | 3 | 1 | 1 |
| 2.9423 | 33 | 2 | 2 | 2 |
| 2.0818 | 7 | 4 | 2 | 2 |
| 1.9547 | 4 | 5 | 1 | 1 |
| 1.7991 | 14 | 4 | 4 | 0 |

Catalyst Preparation for Use

Commercial $CrF_3 \cdot 4H_2O$ (about 54 g) was placed in a gold container and heated to 400° C. for 3 hours. The product was granulated to form 1.2 to 1.7 mm particles for catalytic evaluation. The granulated product was subsequently treated with anhydrous HF at 400° C. for 4 hours as described below. The x-ray diffraction powder pattern of the product was essentially the same as that given for cubic $CrF_3$ in Table 2.

General Procedure for HF Treatment of Cubic $CrF_3$

The granulated catalyst (9.2 g, 10 mL) was placed in a ⅝" (1.58 cm) Inconel® nickel alloy reactor heated in a fluidized sand bath. It was heated to 175° C. in a flow of nitrogen (50 cc/min) at which time HF flow (50 cc/min) was also started through the reactor. After 15 minutes, the nitrogen flow was decreased to 20 cc/min and the HF flow increased to 80 cc/min. The reactor temperature was gradually increased to 400° C. during a 2 hour period and maintained at 400° C. for an additional 30 minutes. At the end of this period the reactor was brought to the desired operating temperature for catalyst evaluation under a nitrogen flow of 10 cc/min and an HF flow of 50 cc/min.

General Procedure for Product Analysis

The following general procedure is illustrative of the method used. Part of the total reactor effluent was sampled on-line for organic product analysis using a Hewlett Packard HP 5890 gas chromatograph equipped with a 20' (6.1 m) long×⅛" (0.32 cm) diameter tubing containing Krytox® perfluorinated polyether on an inert carbon support. The helium flow was 35 mL/min. Gas chromatographic conditions were 70° C. for an initial hold period of three minutes followed by temperature programming to 180° C. at a rate of 6° C./minute. Unless indicated, the reported results are in mole %.

The bulk of the reactor effluent containing organic products and also inorganic acids such as HCl and HF was treated with aqueous caustic prior to disposal.

Legend

| | |
|---|---|
| F115 is $CClF_2CF_3$ | F31 is $CH_2ClF$ |
| F114a is $CCl_2FCF_3$ | F32 is $CH_2F_2$ |
| F113 is $CCl_2FCClF_2$ | F113a is $CCl_3CF_3$ |
| F123 is $CHCl_2CF_3$ | F124 is $CHClFCF_3$ |
| F124a is $CHF_2CClF_2$ | F125 is $CHF_2CF_3$ |
| F134a is $CH_2FCF_3$ | F281ea is $CH_3CHFCH_3$ |
| F227ea is $CF_3CHFCF_3$ | F1112a is $CCl_2=CF_2$ |
| F1123 is $CHF=CF_2$ | F1216 is $CF_3CF=CF_2$ |
| HC1270 is $CH_3CH=CH_2$ | F1316 is $C_4Cl_2F_6$ |

Example 2

Fluorination of Dichloromethane

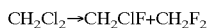
$CH_2Cl_2 \rightarrow CH_2ClF + CH_2F_2$

The General Procedures for HF Treatment of Cubic $CrF_3$ and Product Analysis were used. The HF:dichloromethane molar ratio was 4:1 and the contact time was 15 seconds. Results at various temperatures are shown in Table 3.

TABLE 3

| TEMP. ° C. | F32 | F31 | $CH_2Cl_2$ |
|---|---|---|---|
| 175 | 2.5 | 12.1 | 85.4 |
| 200 | 4.6 | 13.8 | 81.6 |
| 225 | 40.7 | 13.0 | 46.2 |
| 250 | 57.1 | 12.4 | 30.5 |
| 275 | 57.4 | 13.1 | 29.4 |

Example 3

Fluorination of F113a

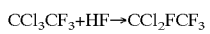
$CCl_3CF_3 + HF \rightarrow CCl_2FCF_3$

The General Procedures for HF Treatment of Cubic $CrF_3$ and Product were used. The organic feed composition to the reactor was 99.8% F113a and 0.2% F114a. The HF:organic ratio was 2:1 and the contact time was 30 seconds. Results at various temperatures are shown in Table 4.

TABLE 4

| TEMP. ° C. | F115 | F114a | F113a | F1112a | OTHERS |
|---|---|---|---|---|---|
| 250 | 0.0 | 0.5 | 98.8 | 0.3 | 0.4 |
| 275 | 0.0 | 1.1 | 98.2 | 0.3 | 0.3 |
| 300 | 0.0 | 4.1 | 95.3 | 0.3 | 0.4 |
| 325 | 0.0 | 8.1 | 91.3 | 0.3 | 0.4 |
| 350 | 0.6 | 86.8 | 12.4 | 0.0 | 0.1 |

Comparative Example A

Fluorination of F113a

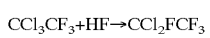
$CCl_3CF_3 + HF \rightarrow CCl_2FCF_3$

The General Procedures for HF Treatment of Cubic $CrF_3$ and Product Analysis were used. However, the catalyst that was used was rhombohedral chromium trifluoride (9.5 g, 10 mL, 12 to 20 mesh (1.68 to 0.84 mm)). The organic feed composition to the reactor was 99.7% F113a and 0.3% F114a. The HF:organic ratio was 2:1 and the contact time was 30 seconds. Results at various temperatures are shown in Table A.

TABLE A

| TEMP. ° C. | F114a | F113 | F1316 | F113a |
|---|---|---|---|---|
| 230 | 0.1 | 0.1 | 1.0 | 98.5 |
| 275 | 0.3 | 0.2 | 0.5 | 98.9 |
| 325 | 4.8 | 0.2 | 0.5 | 94.3 |
| 350 | 24.9 | 0.1 | 0.3 | 74.0 |
| 375 | 32.2 | 0.1 | 0.2 | 67.0 |
| 400 | 60.8 | 0.1 | 0.2 | 38.3 |

Example 4
Disproportionation of F124/F124a $$CHClFCF_3/CHF_2CClF_2 \rightarrow CHCl_2CF_3 + CHF_2CF_3$$

The General Procedures for HF Treatment of Cubic $CrF_3$ and Product Analysis were used. The organic feed composition to the reactor was 98.5% F124 and 1.4% F124a. The contact time was 30 seconds except for the last entry where it was 60 seconds. Results in mole % at various temperatures are shown in Table 5.

TABLE 5

| Temp. (° C.) | %F125 | %F124a | %F124 | %F123 | %Others[a] |
|---|---|---|---|---|---|
| 250 | 0.1 | 1.4 | 98.1 | 0.2 | 0.2 |
| 275 | 0.9 | 1.4 | 96.6 | 1.0 | 0.2 |
| 300 | 35.1 | 0.6 | 29.7 | 33.5 | 1.3 |
| 325 | 39.4 | 0.5 | 23.2 | 34.5 | 2.6 |
| 350 | 44.5 | 0.4 | 18.3 | 30.9 | 6.0 |
| 350 | 46.7 | 0.4 | 17.2 | 28.2 | 8.3 |

[a] Others include $CCl_2=CCl_2$ and $CCl_2=CClF$

Example 5
Hydrofluorination of F1216

$$CF_3CF=CF_2 + HF \rightarrow CF_3CHFCF_3$$

The General Procedures for HF Treatment of Cubic $CrF_3$ and Product Analysis were used. The organic feed composition to the reactor was 99.7% F1216. The HF:organic ratio was 3:1 and the contact time was 15 seconds. Results at various temperatures are shown in Table 6. The first 350° C. run was sampled at 3.5 hours on stream; the second was sampled at 10 hours.

TABLE 6

| Temp. (° C.) | %F1216 | %F227ea | %Others |
|---|---|---|---|
| 300 | 94.5 | 5.2 | 0.2 |
| 325 | 73.3 | 26.3 | 0.3 |
| 350 | 12.2 | 87.2 | 0.5 |
| 350 | 44.0 | 55.6 | 0.3 |

Example 6
Hydrofluorination of HC1270

$$CH_3CH=CH_2 + HF \rightarrow CH_3CHFCH_3$$

The General Procedures for HF Treatment of Cubic $CrF_3$ were used. However the product analysis was done using a GC equipped with a 105 m×0.2 mm ID capillary column coated with 100% dimethyl polysiloxane. All the lines to or from the reactor, i.e., inlet, outlet and valve box were at 50° C. The GC injection port was at 75° C. The organic feed composition to the reactor was 99.5% HC1270. The HF:organic ratio was 4:1 and the contact time was 15 seconds. Results in area% at various temperatures are shown in Table 7.

TABLE 7

| Temp. (° C.) | %HC1270 | %F281ea | %Others |
|---|---|---|---|
| 125 | 29.3 | 69.8 | 0.9 |
| 100 | 27.7 | 72.1 | 0.2 |
| 75 | 43.2 | 56.8 | 0.0 |
| 50 | 53.4 | 46.6 | 0.0 |

Example 7
Hydrofluorination of F1123

$$CHF=CF_2 + HF \rightarrow CH_2FCF_3$$

The General Procedures for HF Treatment of Cubic $CrF_3$ and Product Analysis were used. The organic feed composition to the reactor was 98.9% F1123 and 0.8% F134a. The HF:organic ratio was 4:1 and the contact time was 15 seconds. At 250° C., the products contained 19.5% F1123 and 80.2% F134a.

We claim:

1. A catalytic composition comprising chromium in the form of crystalline chromium fluoride having a cubic crystal structure and having the following X-ray diffraction powder pattern:

| d spacing (Å) | Relative intensity | H | K | L |
|---|---|---|---|---|
| 5.8888 | VS | 1 | 1 | 1 |
| 3.0674 | S | 3 | 1 | 1 |
| 2.9423 | M | 2 | 2 | 2 |
| 2.0818 | W | 4 | 2 | 2 |
| 1.9547 | W | 5 | 1 | 1 |
| 1.7991 | M | 4 | 4 | 0 |

2. The catalytic composition of claim 1 wherein the catalytic composition further comprises other chromium compounds and at least 10 percent of the chromium in the composition is in the form of said cubic chromium trifluoride.

3. In a process for changing the fluorine content of halogenated hydrocarbons containing from one to six carbon atoms, in the presence of a chromium-containing catalyst, the improvement comprising using the catalytic composition of claim 1 as the chromium-containing catalyst.

4. The process of claim 3 wherein a saturated or olefinic compound of the formula $C_nH_aCl_bF_c$, wherein n is an integer from 1 to 6, a is an integer from 0 to 12, b is an integer from 0 to 13 and c is an integer from 0 to 13, provided that b is at least 1 when the compound is saturated, is reacted with HF in the vapor phase in the presence of said catalyst to increase the fluorine content of said compound.

5. The process of claim 3 wherein a compound having the formula $C_pH_gF_hCl$, where p is an integer from 1 to 2, g is an integer from 1 to 3 and h is an integer from 1 to 4, undergoes disproportionation in the presence of said catalyst.

6. The catalytic composition of claim 2, wherein the catalytic composition includes said cubic chromium trifluoride in combination with at least one material selected from the group consisting of magnesium fluoride and zinc fluoride.

7. In a process for changing the fluoride content of halogenated hydrocarbons containing from one to six carbon atoms, in the presence of a chromium-containing catalyst, the improvement comprising using the catalytic composition of claim 6 as the chromium-containing catalyst.

8. A catalytic composition consisting essentially of a crystalline chromium fluoride having a cubic crystal structure with a lattice parameter of 10.201 Angstroms and having the following X-ray diffraction powder pattern:

| d spacing (Å) | Relative intensity | H | K | L |
|---|---|---|---|---|
| 5.8888 | VS | 1 | 1 | 1 |
| 3.0674 | S | 3 | 1 | 1 |
| 2.9423 | M | 2 | 2 | 2 |
| 2.0818 | W | 4 | 2 | 2 |
| 1.9547 | W | 5 | 1 | 1 |
| 1.7991 | M | 4 | 4 | 0 |

9. In a process for changing the fluorine content of halogenated hydrocarbons containing from one to six carbon atoms, in the presence of a chromium-containing catalyst, the improvement comprising using the catalytic composition of claim 8 as the chromium-containing catalyst.

* * * * *